US012778879B2

(12) United States Patent
Kim et al.

(10) Patent No.: US 12,778,879 B2
(45) Date of Patent: Nov. 3, 2026

(54) **COSMETIC COMPOSITION COMPRISING FERMENTED PRODUCT OF *NURUK***

(71) Applicants: DAEBONG LS, LTD, Incheon (KR); COSMOCOS Co., Ltd, Incheon (KR)

(72) Inventors: Ji Hye Kim, Seogwipo-si (KR); Hyun Sook Yeom, Jeju-si (KR); Hye Ja Lee, Seogwipo-si (KR); Kyung Man Hahm, Suwon-si (KR); Jin Oh Park, Seoul (KR); Kyoung Hee Jang, Seoul (KR); Dae Hyun Shin, Incheon (KR); Ho An Kim, Incheon (KR); A Rang Kim, Incheon (KR); DaAe Park, Incheon (KR)

(73) Assignees: DAEBONG LS, LTD, Incheon (KR); COSMOCOS Co., Ltd, Incheon (KR)

( * ) Notice: Subject to any disclaimer, the term of this patent is extended or adjusted under 35 U.S.C. 154(b) by 274 days.

(21) Appl. No.: 17/717,528

(22) Filed: Apr. 11, 2022

(65) Prior Publication Data

US 2022/0378691 A1 Dec. 1, 2022

(30) Foreign Application Priority Data

May 28, 2021 (KR) ........................ 10-2021-0068944

(51) Int. Cl.

*A61K 8/9794* (2017.01)
*A61K 8/9728* (2017.01)
*A61Q 17/00* (2006.01)
*A61Q 19/00* (2006.01)
*A61Q 19/08* (2006.01)

(52) U.S. Cl.

CPC .......... *A61K 8/9794* (2017.08); *A61K 8/9728* (2017.08); *A61Q 17/00* (2013.01); *A61Q 19/005* (2013.01); *A61Q 19/08* (2013.01); *A61K 2800/522* (2013.01); *A61K 2800/85* (2013.01)

(58) Field of Classification Search

None

See application file for complete search history.

(56) References Cited

FOREIGN PATENT DOCUMENTS

| | | | | |
|---|---|---|---|---|
| FR | 2971711 A1 * | 8/2012 | A61K 8/97 |
| KR | 2006033736 A * | 4/2006 | A61K 31/704 |
| KR | 2010105138 A * | 9/2010 | A61K 31/704 |
| KR | 2011018587 A * | 2/2011 | |
| KR | 10 20110034060 A | 4/2011 | |
| KR | 20120071596 A * | 7/2012 | |
| KR | 12681800 B1 | 5/2013 | |
| KR | 20180009968 A * | 1/2018 | |
| KR | 10-2107582 B1 | 5/2020 | |

OTHER PUBLICATIONS

Wikipedia "Anjeunbaengi wheat," last edited Nov. 20, 2023; https://en.wikipedia.org/wiki/Anjeunbaengi_wheat (Year: 2023).*
Kew "*Triticum aestivum* L.," Plants of the World Online, accessed 2024; https://powo.science.kew.org/taxon/urn:lsid:ipni.org:names:332110-2/general-information (Year: 2024).*
Wikipedia "Aspergillus," last edited Feb. 16, 2024; https://en.wikipedia.org/wiki/Aspergillus (Year: 2024).*
Wikipedia "Aspergillus oryzae," last edited Jan. 23, 2024; https://en.wikipedia.org/wiki/Aspergillus_oryzae#:~:text=Aspergillus%20oryzae%2C%20also%20known%20as,making%20soy%20sauce%20and%20miso. (Year: 2024).*
Google translation KR 10-2107582 B1, printed 2023 (Year: 2023).*
Google translation KR 2018-0009968 A, printed 2024 (Year: 2024).*
Google translation KR 2012-0071569 A, printed 2024 (Year: 2024).*
Google translation FR 2971711 A1, printed 2024 (Year: 2024).*
Wikipedia "Nuruk," last edited Apr. 1, 2024; https://en.wikipedia.org/wiki/Nuruk (Year: 2024).*
Google translation KR 2011-0018587 A, printed 2024 (Year: 2024).*
Google translation KR 2010-0105138 A, printed 2024 (Year: 2024).*
Google translation KR 2006-0033736 A, printed 2024 (Year: 2024).*
Cals-Grierson et al. "Nitric oxide function in the skin," Nitric Oxide 10:179-193, 2004 (Year: 2004).*
Chernoff "The utilization of a topical nitric oxide generating serum in the aging skin population: a pilot study," Annals of Plastic and Reconstructive Surgery 4(2): 1053, 2020 (Year: 2020).*
Levin et al. "Atopic dermatitis and the stratum corneum. Part 1: the role of filaggrin in the stratum corneum barrier and atopic skin," Skin Structure and Function 6(10): 16-22, 2013 (Year: 2013).*
Biesebeke et al. "Aspergillus oryzae in solid-state and submerged fermentations. Progress report on a multi-disciplinary project," FEMS Yeast Research 2:245-248, 2002 (Year: 2002).*

* cited by examiner

*Primary Examiner* — Bennett M Celsa
*Assistant Examiner* — Alissa Prosser
(74) *Attorney, Agent, or Firm* — Westman, Champlin & Koehler, P.A.; Amanda M. Prose

(57) ABSTRACT

Provided is a cosmetic composition comprising a fermented product of Nuruk, and particularly, a cosmetic composition that can promote collagen synthesis in skin fibroblasts, have antioxidant effects and moisturizing effects, and prevent aging, comprising a fermented product of Nuruk obtained by fermenting grain with yeast mold (*Aspergillus*), as an active ingredient.

8 Claims, 3 Drawing Sheets

[FIG. 1]
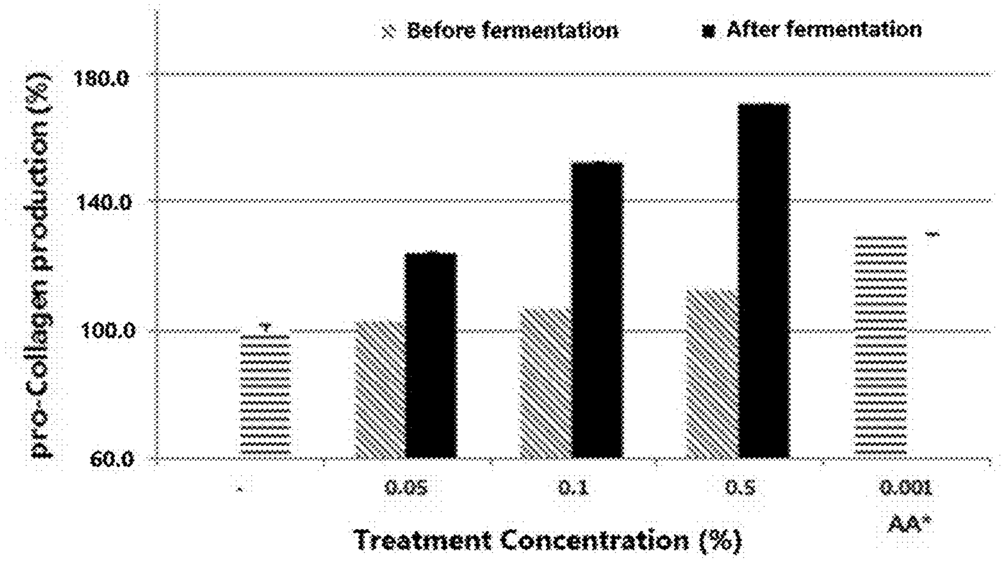
[FIG. 2]
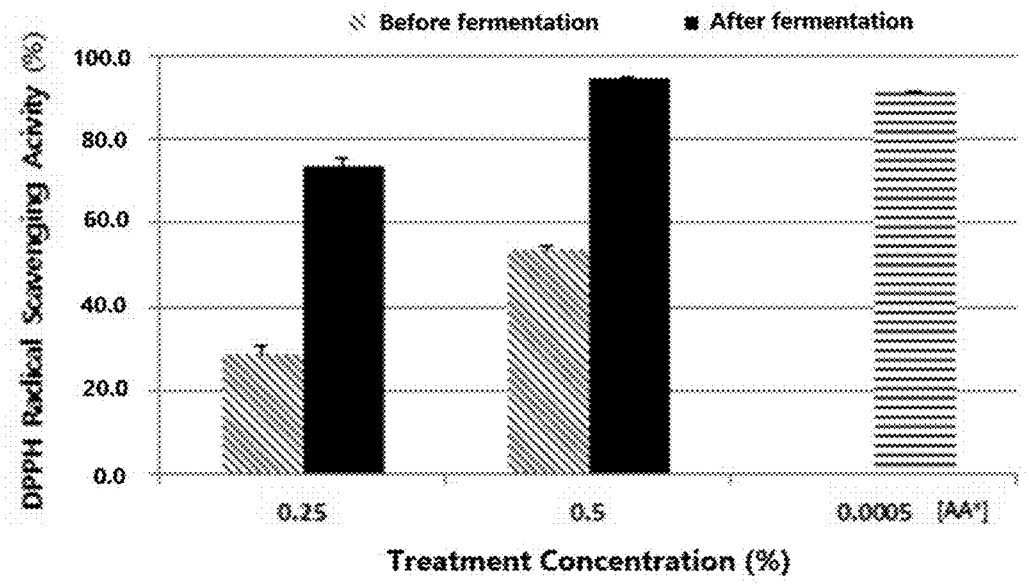

[FIG. 3]
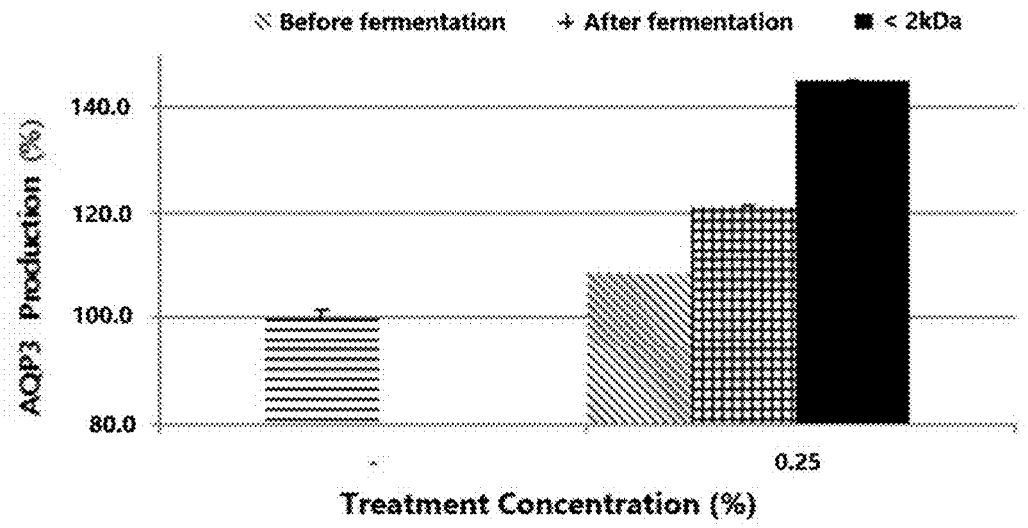
[FIG. 4]
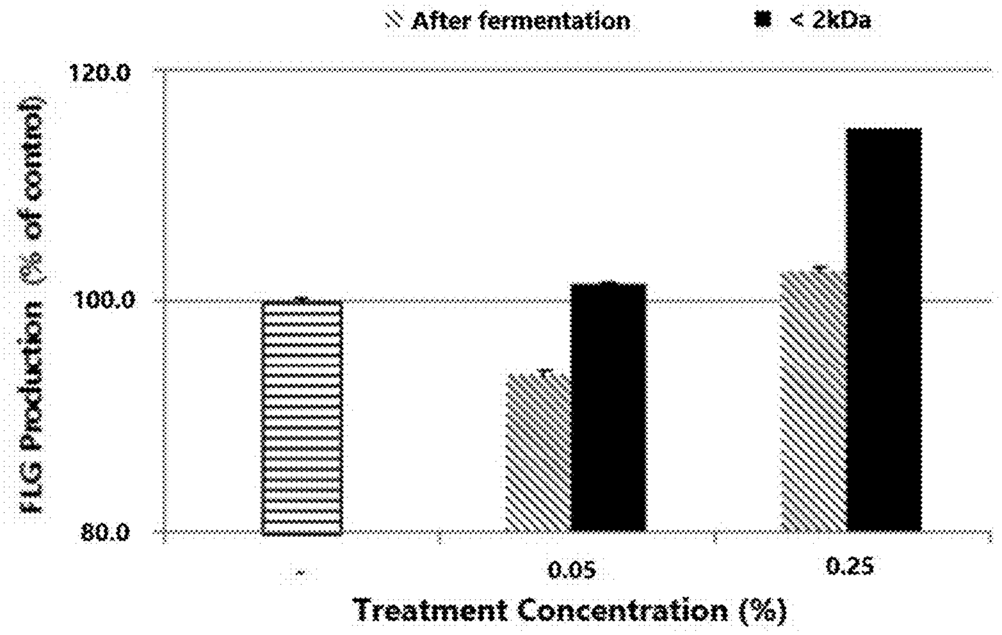

[FIG. 5]
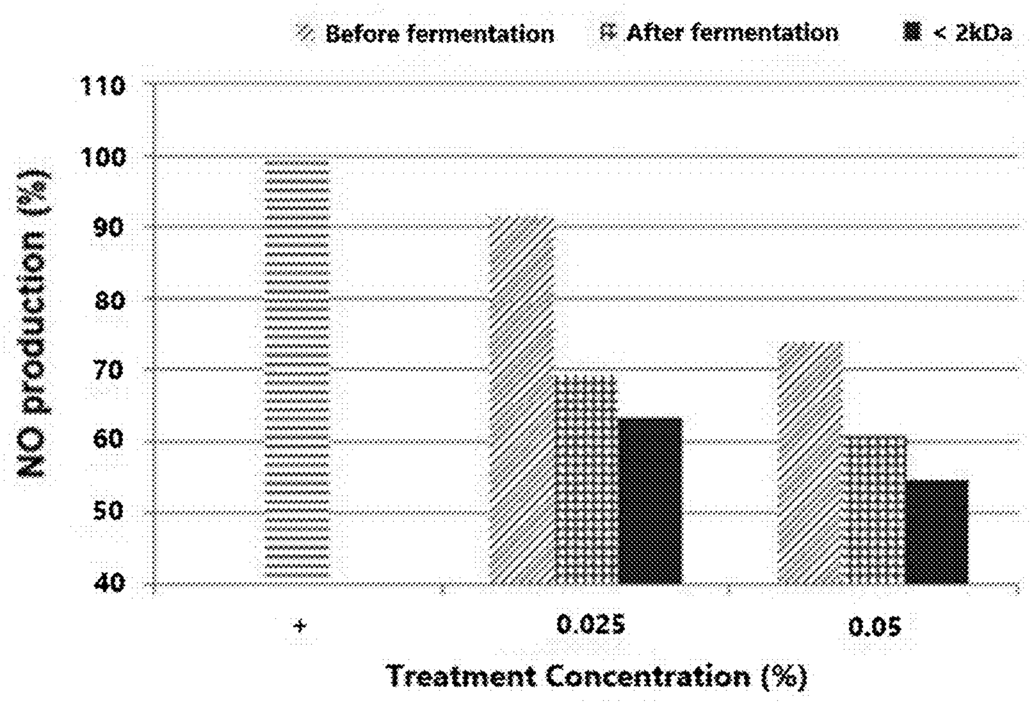

COSMETIC COMPOSITION COMPRISING FERMENTED PRODUCT OF *NURUK*

CROSS REFERENCE TO RELATED APPLICATION

The present application claims priority to Korean Patent Application No. 10-2021-0068944, filed on May 28, 2021, which is hereby incorporated by reference in its entirety.

BACKGROUND OF THE INVENTION

1. Field of the Invention

The present disclosure relates to a cosmetic composition comprising a fermented product of Nuruk.

2. Description of the Related Art

Nuruk is a traditional fermenting agent made by propagating a fungus with alcohol-making enzymes on grains. Nuruk is a natural reproduction of fungi and yeast by grinding grains, which are the main ingredients of alcohol, such as wheat, barley, rice, and millet, whose main ingredient is starch, and kneading them with water to make lumps and propagating a fungus on the lumps. Nuruk is used as a starchy saccharifying agent and fermentation agent.

Since ancient times, based on the fact that people who make rice wine have white and beautiful hands, folk remedies have used skincare using traditional Nuruk or sake lees made from fermented grains. Recently, using natural yeast Nuruk and fermented ingredients of such natural yeast Nuruk, cases of application as a raw material for cosmetics are increasing.

Cosmetic compositions in which natural products such as mulberry leaves, lotus leaves, Duchung, or peony are fermented using Nuruk as a fermented starter have been disclosed in various literature, but there is no case in which a component obtained by fermenting Nuruk itself is applied to a cosmetic composition.

SUMMARY OF THE INVENTION

Therefore, an objective of the present disclosure is to prepare a cosmetic composition comprising a fermented product of Nuruk itself. An objective of the present disclosure is to provide a cosmetic composition that is helpful for skin beauty by utilizing microorganisms including yeast and enzymes contained in large amounts in traditional Nuruk, and various components contained in the raw material of Nuruk, the grain itself.

In order to achieve the above objective, according to an embodiment of the present disclosure, the cosmetic composition comprises a fermented product of Nuruk as an active ingredient. The fermented product of Nuruk is produced by fermenting Nuruk obtained from yeast mold (*Aspergillus*) grown on grains.

The Nuruk may be Nuruk of wheat yeast, barley yeast, rice yeast, mung bean yeast, etc., preferably wheat yeast.

The wheat of the wheat yeast may be, but is not limited to, preferably Anjeunbangi wheat (*Triticum aestivum* L.).

The fermented product of Nuruk may be the one fermented by yeast mold (*Aspergillus*), including yeast yellow mold (*A. oryzae*).

The fermented product of Nuruk may be the one fermented at a temperature of 30 to 50° C.

The fermented product of Nuruk may contain a low molecular weight peptide having a molecular mass of 5 kDa or less and preferably may contain a low molecular weight peptide having a molecular mass of 2 kDa or less.

The fermented product of Nuruk may be used for any one or more of skin wrinkle treatment, skin elasticity improvement, skin soothing, and skin bather strengthening, or as a skin antioxidant.

According to an embodiment of the present disclosure, a method for preparing a cosmetic composition comprising a fermented product of Nuruk as an active ingredient comprises filtering the fermented product of Nuruk through a 2 kDa filtration membrane.

The method may comprise a step of fermenting Nuruk at a temperature of 30 to 50° C. to obtain a fermented product of Nuruk before the filtration step.

The fermented product of Nuruk, according to an embodiment of the present disclosure, may contain a peptide having a molecular mass of 2 kDa or less and may be the one prepared by immersion-fermentation of wheat yeast Nuruk.

The method for producing a fermented product of Nuruk, according to an embodiment of the present disclosure, may comprise: preparing a fermented product of Nuruk by immersion-fermentation of Nuruk at a temperature of 30 to 50° C. for 3 to 5 days; and filtering the fermented product of Nuruk through a 2 kDa filtration membrane.

The cosmetic composition of the present disclosure comprises a fermented product of Nuruk as an active ingredient. The fermented product of Nuruk can be absorbed into skin to promote collagen synthesis in skin fibroblasts and can exhibit antioxidant efficacy by increasing free radical scavenging activity and moisturizing efficacy by increasing the production amount of Aquaporin 3 and filaggrin, and the production of nitrogen monoxide can be suppressed. Therefore, the fermented product of Nuruk can be used for a cosmetic composition that is safe for the human body and effective in improving a user's skin condition.

BRIEF DESCRIPTION OF THE DRAWINGS

FIG. 1 is a graph showing comparative results of the procollagen synthesis effect (PIP, procollagen production amount, %) according to the treatment concentration before fermentation of Nuruk (Comparative Example 1) and after fermentation of Nuruk (Example 1);

FIG. 2 is a graph showing comparative results of DPPH radical scavenging activity (%) according to the treatment concentration of before fermentation of Nuruk (Comparative Example 1) and after fermentation (Example 1);

FIG. 3 is a graph showing the comparative results of Aquaporin 3 Production amount according to the treatment concentration before fermentation of Nuruk (Comparative Example 1), after fermentation of Nuruk (Example 1) and after fermentation and filtration 2 kDa, Example 2);

FIG. 4 is a graph showing comparative results of filaggrin production (FLG production) according to the treatment concentration after fermentation of Nuruk (Example 1) and after fermentation and filtration of Nuruk (<2 kDa, Example 2);

FIG. 5 is a graph showing comparative results of nitrogen monoxide (NO) production according to the treatment concentration after fermentation of Nuruk (Example 1) and after fermentation and filtration treatment of Nuruk (<2 kDa, Example 2).

DESCRIPTION OF THE PREFERRED EMBODIMENTS

'Nuruk' refers to the one obtained by culturing and propagating yeast mold (*Aspergillus*) on grains.

In the present disclosure, 'fermentation' refers to a process of liquid-fermentation of Nuruk in water and decomposition of organic matter in grains by microorganisms, that is, yeast mold.

Hereinafter, embodiments of the present disclosure will be described in detail with reference to the accompanying drawings so that those of ordinary skilled in the art to which the present disclosure pertains can easily perform the present disclosure. However, the present disclosure may be embodied in many different forms and is not limited to the embodiments and drawings described herein.

According to one embodiment of the present disclosure, the cosmetic composition comprises a fermented product of Nuruk as an active ingredient.

The cosmetic composition has an excellent effect of improving a user's skin condition through collagen synthesis, an antioxidant effect through free radical scavenging activity, an increase in skin moisture by increasing aquaporin 3 (AQP3) and filaggrin (FLG) that holds skin moisture and a suppressing effect of the production of nitrogen monoxide causing skin aging. Further, since active ingredients of the cosmetic composition are natural substances, the composition does not cause problems related to resistance and safety. Accordingly, the cosmetic composition of the present disclosure has excellent effects such as anti-aging, anti-inflammation, skin soothing, skin bather strengthening, wrinkle treatment, elasticity improvement, etc. It can be useful for improving a user's skin conditions, for example, skin wrinkles, elasticity, moisturizing conditions, and inflammatory conditions. The cosmetic composition of the present disclosure can be widely used in the manufacture of various cosmetics, such as being used as a cosmetic composition for at least one of skin wrinkle treatment, skin elasticity improvement, skin soothing, skin bather strengthening, anti-aging, and anti-inflammation use.

The fermented product of Nuruk of the present disclosure is a fermented product prepared by using the Nuruk itself. That is, the fermented product of Nuruk is a fermented product obtained by re-fermenting the Nuruk already produced by fermentation of grains. The fermented product of Nuruk comprises natural substances such as starch and minerals contained in wheat, raw materials for Nuruk, as well as natural microorganisms including yeast and enzymes contained in Nuruk, and products formed by fermentation with the microorganisms, which provides excellent effects on improving skin condition.

The Nuruk may be prepared not only by the traditional method of manufacturing by natural fermentation of grains, but also by all types of Nuruk production methods, such as fermentation and then aging and drying, in which the grain is pulverized and mixed with yeast mold (*Aspergillus*) with an appropriate amount of moisture, put in a Nuruk molding ring, molded by hand, or put in a sack or bale, tied with a spout, and then in a yeast room (fermentation room) where proper temperature and humidity are maintained.

The Nuruk may be made from any one selected from the group consisting of rice, glutinous rice, barley, wheat, bran, brown rice, oats, perilla, millet, barley, buckwheat, millet, mung bean and red bean, or a mixture of two or more thereof as a raw material, but is not limited thereto. The Nuruk may be made preferably from wheat, and more preferably, from Anjeunbaengi wheat (*Triticum aestivum* L.), a native variety native to Korea, which has a higher protein content than other varieties and has a lower gluten content than general wheat, which can cause skin troubles such as atopy.

The fermented product of Nuruk may be fermented by fungus of yeast mold (*Aspergillus*), wherein the fungus may be at least one selected from the group consisting of black mold (*A. niger*), white yeast infection (*A. luchuensis*), yeast yellow mold (*A. oryzae*), and black yeast mold (*A. awamori*), but is not limited thereto. In the following Example of the present disclosure, Nuruk fungus cultured in Anjeunbaengi wheat yeast was used, and yeast yellow mold (*A. oryzae*) is generally most distributed in the cultured Nuruk fungus.

The fermented product of Nuruk may be fermented at a temperature of 30 to 50° C., preferably 30 to 40° C., for example 32 to 37° C., in which yeast mold (*Aspergillus*) may be most activated. If the fermentation temperature is less than 30° C., the yeast may not be fermented appropriately, and if it exceeds 50° C., it may become over-fermented and may not exhibit sufficient efficacy.

The fermented product of Nuruk may have an excellent skin improvement effect when including peptide having a low molecular weight, preferably a molecular mass of peptide may be 5 kDa or less, more preferably a molecular mass of peptide may be 3 kDa or less, and most preferably, when the molecular mass of the peptide is 2 kDa or less, the skin improvement effect may be more excellent. If the molecular mass of peptide exceeds 5 kDa, the skin penetration rate may be low, and thus a sufficient effect cannot be exerted.

Another aspect of the present disclosure is a method for preparing a fermented product of Nuruk.

A fermented product of Nuruk of the present disclosure is prepared by fermenting Nuruk in water, also called immersion fermentation, and growing microorganisms in a liquid environment, unlike solid fermentation.

The fermented product of Nuruk may be prepared by performing a fermentation process in water (purified water) with Nuruk prepared by a traditional yeast preparation method of naturally proliferating yeast fungi on grains such as wheat or Nuruk prepared by mixing and culturing wheat and yeast mold. The fermented product of Nuruk can also be produced by directly mixing and fermenting wheat powder with a separate yeast mold in purified water.

In the fermentation, by controlling the temperature, time, pH, agitation degree, oxygen concentration, etc., nutrients are evenly supplied to the entire microorganism to promote the growth of microorganisms and fermentation.

The fermented product of Nuruk may be fermented at a temperature of 30 to 50° C., preferably 30 to 40° C., for example 32 to 37° C., in which yeast mold (*Aspergillus*) may be most activated. If the fermentation temperature is less than 30° C., the yeast may not be fermented appropriately, and if it exceeds 50° C., it may become over-fermented and may not exhibit sufficient efficacy.

The fermentation period is 3 to 10 days, preferably 5 to 7 days, but may be appropriately adjusted according to the fermentation temperature. If the fermentation period is too short, fermentation is not performed properly, and if the fermentation period is too long, it may be over-fermented and adversely affect the user's skin condition.

The fermented product of Nuruk may further improve the effect by controlling the size of the peptide through centrifugation and/or filtration using a filtration membrane, and may be filtered through a filtration membrane having a pore size of 5 kDa or less, preferably 3 kDa or less, more preferably 2 kDa or less. When the pore size of the filtration membrane exceeds 5 KDa, the skin penetration rate of the peptide is low, and thus a sufficient effect may not be exerted.

The fermented product of Nuruk, according to the present disclosure, may promote collagen synthesis in skin fibroblasts, exhibit antioxidant efficacy through increased free radical scavenging activity, and increase production of aquaporin 3 and filaggrin to exhibit a moisturizing effect. The fermented product of Nuruk may suppress skin aging by inhibiting the production of nitrogen monoxide and is safe for the human body. The fermented product of Nuruk of the present disclosure may be used as an effective composition for external application to the skin for improving a user's skin condition, specifically antioxidants such as anti-inflammation or anti-aging, moisturizing, skin soothing, skin bather strengthening, wrinkle treatment, elasticity improvement, etc. Therefore, it is possible to prepare a fermented product of Nuruk in the same manner as described above, and to prepare a cosmetic composition including the prepared fermented product of Nuruk as an active ingredient.

The cosmetic composition of the present disclosure may be formulated in any formulation commonly prepared in the art, specifically, a formulation for skin care, body care, or makeup. The cosmetic composition of the present disclosure may be formulated as, creams, lotions, skin toner, essences, emulsions, powders, packs, foundations, lipsticks, cleansing lotions, cleansing foams, body cleansers, and the like.

In addition, the cosmetic composition of the present disclosure may comprise a cosmetically or dermatologically acceptable medium, for example, water, an alcoholic solvent, etc., in addition to the fermented product of Nuruk. In addition, the cosmetic composition of the present disclosure may further include one or more adjuvants such as surfactants, preservatives, pH adjusters, thickeners, emulsifiers, fillers, pigments, fragrances, moisturizers, and chelating agents.

Hereinafter, the present disclosure will be described in more detail through specific examples. The following examples are intended to illustrate the present disclosure, but the present disclosure is not limited by the following examples.

Preparation Example: Preparation of a Fermented Product of Nuruk

Example 1

After adding 10 times the weight of purified water based on the weight of the Nuruk to the Anjeunbangi wheat Nuruk (purchased by Jinju-si Gokja Industrial Research Institute), the Nuruk was fermented at a temperature of 37° C. for 5 to 7 days to prepare a fermented product of Nuruk. The fermented product of Nuruk was suspended in purified water 3 times the weight of the fermented product of Nuruk, and the suspension was filtered through a 5 μm filter.

Then, the filtrate was concentrated under reduced pressure until it became 10 brix and then filtered through a 0.45 μm filter to obtain a fermented product of Nuruk.

Example 2

The concentrated fermented product of Nuruk obtained in Example 1 was mixed with ethanol three times the weight of the concentrated fermented product of Nuruk and reacted at 4° C. for 24 hours.

Thereafter, in order to remove ethanol, the resultant product was concentrated under reduced pressure until it reached 10 brix.

Then, it was centrifuged for 70 minutes at 3000×g (gravity) using Ultra Filtration (UF) with a 2 kDa filter.

After centrifugation, a lower part sample of 2 kDa or less was separated, and 1 N of NaOH was added to adjust the pH to 6.00, and then citric acid was added to reach pH 3.99, and then filtered with a 0.45 filter to obtain a fermented product of Nuruk including 2 kDa or less peptides (Example 2).

Comparative Example 1

For comparison with the fermented product of Nuruk, after adding 10 times the weight of purified water based on the weight of the Nuruk to the Anjeunbangi wheat Nuruk (purchased by Jinju-si Gokja Industrial Research Institute), the Nuruk was extracted at a temperature of 37° C. for 1 to 3 hours to obtain Nuruk extract.

Thereafter, the obtained Nuruk extract was filtered through a 0.45 μm filter to obtain Nuruk extract without additional fermentation (Comparative Example 1).

Experimental Example 1: Cell Culture

The cells used in Experimental Examples 2 to 7 were used after cell culture through the following culture method.

(Culturing Human Epidermal Keratinocytes)

HaCaT cells, which are human epidermal keratinocytes, were purchased from Cell Line service GmbH (Germany). The cells were cultured in a 37° C., 5% $CO_2$ thermostat using a DMEM (Dulbecco's Modified Egg's Medium) medium containing 1% penicillin-streptomycin and 10% fetal bovine serum (FBS), and subculture was performed at intervals of 2 to 3 days.

(Cultivation of Dermal Fibroblasts)

Normal Human Dermal Fibroblasts (NHDF) cells, which are dermal fibroblasts, were purchased from Lonza (Lonza Walkersville, Inc) and used.

The cells were cultured in a 37° C., 5% $CO_2$ thermostat using Fibroblast Basal Medium (FBM) medium containing 0.1% hFGF-B, insulin, GA-1000, and 2% fetal bovine serum, and subculture was performed at intervals of 2 to 3 days.

(Macrophage Culture)

Macrophages, RAW264.7 cells, were purchased from American Type Cell Culture (ATCC) and used. The cells were cultured in a 37° C., 5% $CO_2$ thermostat using a DMEM (Dulbecco's Modified Egg's Medium) medium containing 1% penicillin-streptomycin and 10% fetal bovine serum (FBS), and subculture was performed at intervals of 2 to 3 days.

Experimental Example 2: Evaluation of Cytotoxicity to Macrophages

Ez-cytox assay is a representative method for measuring cell viability using the principle that water solution tetrazolium salt (WST) reacts with dehydrogenase of living cells to form orange water-soluble Formazan.

In order to check the toxicity in cells, RAW264.7 cells were aliquoted into a 96 well plate at $1.5\times10^4$ cells/well using a cultured DMEM medium with 10% FBS added and incubated for 18 hours at 37° C., 5% $CO_2$ conditions.

The cultured cells were exchanged with a serum-free DMEM medium, and the prepared fermented product of Nuruk (Example 1) was treated to have a concentration of 0.025% and 0.05% (v/v), respectively. Thereafter, EZ-cytox was added to each well and reacted at 37° C. and 5% $CO_2$ for 30 minutes, and then absorbance was measured at 450 nm using a microplate reader. The average absorbance value for each sample group was obtained, and the cell viability was evaluated by comparing it with the absorbance value of the untreated group.

In addition, the Nuruk extract (Comparative Example 1) was treated to have concentrations of 0.025% and 0.05% (v/v), respectively, and absorbance values of Examples 1 and 2 were also measured by the same experimental method.

TABLE 1

| | Cytotoxicity | |
|---|---|---|
| | Treatment concentration (%) | RAW264.7 Cell growth rate (%) |
| Untreated group | — | 94.0 ± 1.5 |
| Stimulant (LPS) | 1 μg/mL | 100.0 ± 3.3 |
| Comparative Example 1 | 0.025 | 93.9 ± 6.0 |
| | 0.05 | 95.9 ± 2.7 |
| Example 1 | 0.025 | 105.3 ± 3.5 |
| | 0.05 | 107.1 ± 3.0 |
| Example 2 | 0.025 | 104.3 ± 6.9 |
| | 0.05 | 111.5 ± 2.3 |

Referring to Table 1 above, cytotoxicity to macrophages in all samples was not observed.

Experimental Example 3: Collagen Synthesis Effect

NHDF fibroblasts were aliquoted into $2.0\times10^4$ cells/well in a 24 well plate and then cultured for 24 hours under cell culture conditions.

After exchanging the medium of the cultured cells with a serum-free FBM medium, the samples prepared in Example 1 and Comparative Example 1 were treated to a concentration of 0.1 and 0.5 v/v %, respectively, and cultured for 24 hours.

Thereafter, the supernatant of each experimental group (Example 1 and Comparative Example 1) was taken to measure the amount of pro-collagen released into the medium. The amount of procollagen was measured using a procollagen type I peptide (PIP) EIA kit (Takara Biomedical Co.) and was performed according to the method provided by the manufacturer. The amount of procollagen type 1 peptide production according to the treatment of the fermented product of Nuruk (Example 1) and the Nuruk extract (Comparative Example 1) are shown in Table 2 and FIG. 1.

TABLE 2

| | Treatment concentration (%) | PIP production (%) |
|---|---|---|
| Untreated group | — | 100 ± 1.44 |
| Comparative Example 1 | 0.1 | 106.43 ± 6.13 |
| | 0.5 | 112.56 ± 1.56 |
| Example 1 | 0.1 | 152.35 ± 0.4 |
| | 0.5 | 170.55 ± 0.23 |

Referring to Table 2 and FIG. 1, it can be seen that the collagen synthesis effect of the fermented product of Nuruk of the present disclosure is excellent because the amount of PIP production in Example 1 (after fermentation) is more than that of Comparative Example 1 (before Fermentation) extracted without fermenting the Nuruk.

Experimental Example 4: Antioxidant Effect

The free radical scavenging test uses that the absorbance of stable DPPH shows the maximum absorbance at 517 nm, and as the free radical DPPH is removed by the sample and turns from purple to pale yellow, that is, as the free radical scavenging rate increases, the absorbance at a 517 nm decreased. The following assay test method was performed by applying the decrease in absorbance at 517 nm wavelength.

First, the fermented product of Nuruk (Example 1) was diluted with methanol to have a concentration of 0.25% and 0.5%, respectively, to prepare a dilution solution of fermented product of Nuruk. A sample was prepared by mixing 1 ml of the dilution solution of the fermented product of Nuruk and 1 ml of a 0.1 mM 2,2-diphenyl-1-picryl-hydrazyl radical (DPPH, Sigma) solution. After leaving the prepared sample at room temperature for 15 minutes, absorbance was measured at a wavelength of a 517 nm using a microplate reader.

Then, for Nuruk extract (Comparative Example 1), the absorbance was measured in the same manner as in the experimental method for the Examples, except that those diluted with methanol were used so that the concentrations of the Nuruk extract (Comparative Example 1) were 0.25% and 0.5%, respectively.

In addition, a mixed solution of 1 ml of DPPH and 1 ml of methanol was used for the negative control, and a mixed solution of 1 ml of methanol and 1 ml of the sample was used as a blank sample for obtaining each color correction value for the sample and the control. In addition, the positive control of this experimental example was prepared by mixing 1 ml of ascorbic acid (10 ppm) solution diluted in methanol and 1 ml of DPPH.

TABLE 3

| | Treatment concentration (%) | DPPF radical scavenging activity (%) |
|---|---|---|
| Untreated group | — | 0 ± 2.4 |
| Comparative Example 1 | 0.25 | 28.66 ± 2.04 |
| | 0.5 | 53.51 ± 1.01 |
| Example 1 | 0.25 | 73.51 ± 2.15 |
| | 0.5 | 94.61 ± 0.11 |
| Ascorbic acid | 0.0005 | 91.36 ± 0.13 |

Referring to Table 3, which shows a result of measuring the antioxidant effect, it may be confirmed that Example 1 of the fermented product of Nuruk has a superior radical scavenging effect compared to Comparative Example 1, and the radical scavenging activity increases as the concentration of the fermented product of Nuruk increases. In Table 3, DPPH radical scavenging activity (%) according to treatment concentrations for Comparative Example 1 and Example 1 is shown in FIG. 2.

Experimental Example 5: Effect of Increasing the Production Amount of Moisturizing Factor Aquaporin 3 (AQP3)

HaCaT cells were aliquoted into a 24 well plate at $1.0\times10^5$ cells/well and cultured for 18 hours at 37° C. and 5% $CO_2$ conditions. The cultured cell medium was exchanged with a serum-free DMEM medium, and the fermented product of Nuruk (Example 1) was treated to have a concentration of 0.1% and 0.25% (v/v), respectively, and cultured for 24 hours. In addition, the treatment concentration of fermented product of Nuruk of Example 2 (including protein of only 2 kDa or less) separated by protein size was 0.25% (v/v) and cultured for 24 hours.

After dissolving the cells of each group, the protein was taken, and the Aquaporin 3 production amount in the culture extract was measured.

Aquaporin 3 production amount was measured using the AQP3-ELISA kit (Elabscience Biotechnology Co., Ltd) and was performed by the method provided by the manufacturer.

And the Nuruk extract (Comparative Example 1) was treated to have a concentration of 0.10% and 0.25% (v/v), respectively. In addition, the negative control group was not treated with any extract (untreated group).

The results of Experimental Example 5 are shown in Table 4 and FIG. 3.

TABLE 4

| | Treatment concentration (%) | AQP3 production (%) |
|---|---|---|
| Untreated group | — | 100 ± 0.21 |
| Comparative Example 1 | 0.25 | 108.47 ± 0.04 |
| Example 1 | 0.25 | 121.14 ± 0.46 |
| Example 2 | 0.25 | 145.43 ± 0.12 |

Referring to Table 4 and FIG. 3, which shows a result of measuring the amount of production of AQP3, a skin moisturizing factor, it may be seen that the fermented product of Nuruk of Examples exhibits an excellent amount of moisturizing factor production compared to Comparative Example.

In addition, the fermented product of Nuruk of Example 2, in which the fermented product of Nuruk of Example 1 is composed of only a protein of 2 kDa or less through centrifugation and filtration processes, showed the best production amount of AQP3 when the concentration was 0.25%.

Experimental Example 6: Effect of Increasing the Production of the Moisturizing Factor Filaggrin (FLG)

HaCaT cells were aliquoted into a 24 well plate at $1.0\times10^5$ cells/well and cultured for 18 hours at 37° C. and 5% $CO_2$ conditions.

After exchanging the medium of the cultured cells with a serum-free DMEM medium, Examples 1 and 2 prepared in Preparation Examples were treated to have concentrations of 0.05 and 0.25 v/v %, respectively, and cultured for 24 hours.

After dissolving the cells of each experimental group, the protein was taken, and the amount of filaggrin produced in the culture extract was measured. The control group was treated with retinoic acid at a concentration of 10 µM.

The filaggrin production amount was measured using the Filaggrin-ELISA kit (Cusabio Biotechnology Co., Ltd), and was performed by the method provided by the manufacturer. Table 5 and FIG. 4 show the results of measurement of filaggrin production according to the filtration treatment of fermented product of Nuruk.

TABLE 5

| | Treatment concentration (%) | FLG production (%) |
|---|---|---|
| Control | — | 100 ± 0.17 |
| Example 1 | 0.05 | 93.48 ± 0.11 |
| | 0.25 | 102.58 ± 0.22 |
| Example 2 | 0.05 | 101.49 ± 0.28 |
| | 0.25 | 114.76 ± 0.12 |

As shown in Table 5 and FIG. 4, it may be seen that the increased rate of the filaggrin production of Example 2 is superior to that of Example 1.

Experimental Example 7: Nitrogen Monoxide (NO) Production Inhibitory Activity RAW264.7 cells were aliquoted into a 24 well plate at $1.0\times10^5$ cells/well and cultured for 18 hours at 37° C. and 5% $CO_2$ conditions.

After exchanging the medium of the cultured cells with a serum-free DMEM medium, Examples 1 to 2 and Comparative Example 1 prepared in Preparation Examples were treated to have concentrations of 0.025 and 0.05 v/v %, respectively, and cultured for 24 hours.

After 100 uL of the supernatant from each experimental group was obtained, 100 uL of Griess reagent was added and reacted at room temperature for 10 minutes. Then, the absorbance was measured at a 540 nm using a microplate reader. Relative results of NO production according to the treatment of Examples 1 to 2 and Comparative Example 1 prepared in Preparation Example were measured based on the NO production amount of the stimulant (LPS), and are shown in Table 6 and FIG. 5.

TABLE 6

| | Treatment concentration (%) | Nitrogen monoxide production (%) |
|---|---|---|
| Stimulant (LPS) | 1 µg/mL | 100 ± 4.24 |
| Comparative Example 1 | 0.025 | 91.57 ± 6 |
| | 0.05 | 73.73 ± 1.99 |
| Example 1 | 0.025 | 69.21 ± 0.93 |
| | 0.05 | 60.85 ± 3.67 |
| Example 2 | 0.03 | 63.12 ± 0.54 |
| | 0.05 | 54.56 ± 0.78 |

As shown in FIG. 5, it was confirmed that Example 1 further suppressed NO production than Comparative Example 1, and the fermented product of Nuruk (Example 2) composed of low molecules of less than 2 kDa further suppressed NO production.

Overall, the present inventors prepared a fermented product of Nuruk fermented using yeast mold and confirmed that the fermented product of Nuruk is not cytotoxic but also has a collagen synthesis effect, an antioxidant effect, an effect of increasing the amount of moisturizing factor production, and an inhibition effect on nitrogen monoxide production. This means that antioxidant, skin moisturizing, and wrinkle treatment effects are excellent. The fermented product of Nuruk extract of the present disclosure may be used in various fields such as cosmetics and food to improve a user's skin condition.

The above description is merely an example of the present disclosure, and it will be appreciated by those skilled in the art that the present disclosure may be implemented in a modified form within a range that does not deviate from the essential characteristics of the present disclosure. Therefore, the disclosed embodiments and experimental examples should be considered from an illustrative rather than a restrictive point of view. The scope of the present disclosure is indicated in the claims rather than the foregoing description, and all differences within the scope equivalent thereto should be construed as being included in the present disclosure.

What is claimed is:

1. A cosmetic composition comprising a fermented product of Nuruk as an active ingredient, wherein the fermented product of Nuruk is a fermented product obtained by re-fermenting the Nuruk produced by fermentation of grain, wherein the fermented product of Nuruk is obtained by a method comprising the steps of:

(a) fermenting for 5 to 7 days at a temperature of 30 to 50° C.;

(b) centrifuging the Nuruk fermentation mixture for 70 minutes at 3000×g using ultrafiltration (UF) with a 2 kDa membrane;

(c) separating the lower-phase fraction containing peptides having a molecular weight of 2 kDa or less;

(d) adjusting the pH of the separated fraction to 6 by adding sodium hydroxide (NaOH);

(e) further adjusting the pH by adding citric acid; and (f) filtering the resulting solution through a 0.45 μm filter to obtain the fermented product of Nuruk comprising peptides having a molecular weight of 2 kDa or less.

2. The cosmetic composition of claim 1, wherein the Nuruk is wheat yeast Nuruk.

3. The cosmetic composition of claim 2, wherein the wheat of the wheat yeast Nuruk is *Triticum aestivum* L.

4. The cosmetic composition of claim 1, wherein the fermented product of Nuruk is obtained by fermenting with *Aspergillus* including *A. oryzae*.

5. The cosmetic composition of claim 1, wherein the cosmetic composition is effective in the treatment of skin wrinkles or to improve skin elasticity.

6. The cosmetic composition of claim 1, wherein the cosmetic composition is effective for skin soothing.

7. The cosmetic composition of claim 1, wherein the cosmetic composition is effective for strengthening the skin barrier.

8. The cosmetic composition of claim 1, wherein the cosmetic composition is a skin antioxidant.

* * * * *